United States Patent [19]

Eckstein

[11] Patent Number: 4,563,532
[45] Date of Patent: Jan. 7, 1986

[54] PROCESS FOR THE PREPARATION OF $\Delta^4$-1,3,4-OXADIAZOLIN-2-ONE COMPOUNDS

[75] Inventor: Udo Eckstein, Cologne, Fed. Rep. of Germany

[73] Assignee: Bayer Aktiengesellschaft, Leverkusen, Fed. Rep. of Germany

[21] Appl. No.: 556,715

[22] Filed: Nov. 30, 1983

[30] Foreign Application Priority Data

Dec. 7, 1982 [DE] Fed. Rep. of Germany ....... 3245202

[51] Int. Cl.⁴ .......................................... C07D 271/10
[52] U.S. Cl. .................................................. 548/144
[58] Field of Search ......................................... 548/144

[56] References Cited

U.S. PATENT DOCUMENTS 4,246,403  1/1981  Prossel ................................ 542/432

*Primary Examiner*—Robert Gerstl
*Attorney, Agent, or Firm*—Sprung, Horn, Kramer & Woods

[57] ABSTRACT

Optical brighteners of the formula

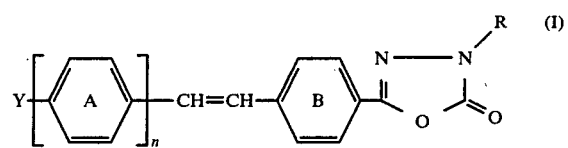

wherein
Y denotes a carbocyclic or heterocyclic radical,
R denotes hydrogen or $R_1$,
wherein
$R_1$ is an optionally substituted alkyl, aralkyl or aryl radical, and
n denotes 0 or 1 and
the rings A and B can carry further substituents, are obtained in a simple manner by a process in which compounds of the formula

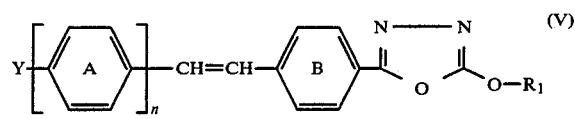

are rearranged at elevated temperatures—if appropriate in the presence of acids.

2 Claims, No Drawings

PROCESS FOR THE PREPARATION OF Δ⁴-1,3,4-OXADIAZOLIN-2-ONE COMPOUNDS

The present invention relates to a new process for the preparation of compounds of the formula

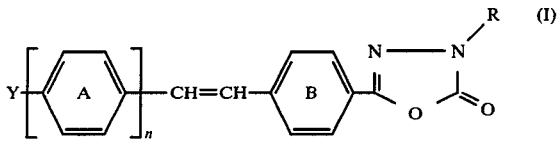
(I)

wherein
- Y denotes a carbocyclic or heterocyclic aromatic radical,
- R denotes hydrogen or $R_1$,
- $R_1$ denotes an optionally substituted alkyl, aralkyl or aryl radical, and
- n denotes 0 or 1 and
- the rings A and B can carry further non-chromophoric substituents.

Some of the compounds of the formula I, which are useful optical brighteners, are known (compare German Offenlegungsschrift No. 2,833,470). According to this patent publication, these compounds are prepared either by reacting acid hydrazides of the formula

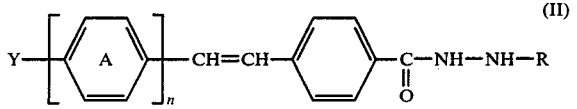
(II)

with phosgene or chloroformates, or by condensing compounds of the formula

(III)

with a compound of the formula

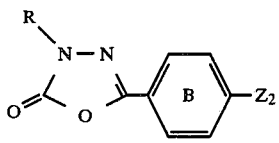
(IV)

wherein
- $Z_1$ and $Z_2$ are the conventional functional groups suitable for formation of —CH=CH— bridges.

However, these processes have the disadvantages that they are not universally applicable (for example, compounds of the formula II in which R=alkyl cannot be prepared or can be prepared only with difficulty), or that the starting materials of the formulae III and IV can be obtained on an industrial scale only with a relatively high expenditure.

It has now been found that the compounds of the formula I can be prepared in a simple and economical manner by a process in which compounds of the formula

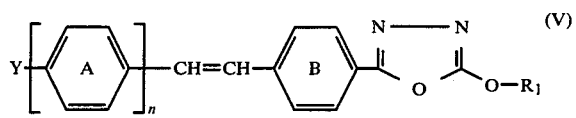
(V)

are rearranged at temperatures of 100°–250° C.—if appropriate in the presence of acids.

This heat-induced rearrangement proceeds surprisingly selectively, with migration of the radical $R_1$ from the oxygen to the adjacent, more nucleophilic nitrogen.

The non-chromophoric substituents optionally present in the compounds of the formula I are the conventional non-chromophoric substituents of brightener chemistry, that is to say, for example, $C_1$–$C_4$-alkyl, $C_1$–$C_4$-alkoxy, phenyl, phenoxy or Cl. However, the rings A and B are preferably unsubstituted.

Suitable aromatic carbocyclic radicals Y are aryl radicals as defined below in more detail.

Suitable quasi-aromatic heterocyclic radicals Y are radicals of 5-membered or 6-membered mono-, di- or tri-nuclear heterocyclic compounds, such as, for example, those of the oxazole, imidazole, 1,2,4-oxadiazole, 1,3,4-oxadiazole, 1,3,4-thiadiazole, 1,2,3-, 1,2,4- and 1,3,4-triazole, pyrimidine, 1,3,5-triazine, benzoxazole, benzothiazole, benzimidazole, naphthoxazole, benzo-s-triazole, naphtho-s-triazole, benzo(b)-furan, quinazoline or quinoxaline series, which are linked with the remainder of the molecule in a conventional manner.

Radicals from the benzoxazole, benzo(b)-furan, benzo-s-triazole, naphtho-s-triazole, 1,2,4- and 1,3,4-oxadiazole, 1,2,3-, 1,2,4- and 1,3,4-triazole and 1,3,5-triazine series are particularly preferred.

Suitable non-chromophoric substituents are R, OH, CN, OR, COR, $SO_2R$, NHCOR, $CONH_2$, $NHSO_2R$, OCOR, COOR, COOH, NHR', $SO_3H$ and the like.

Alkyl is, in particular, $C_1$–$C_6$-alkyl, which can be substituted by hydroxyl, $C_1$–$C_4$-alkoxy, CN, carboxyl, $C_1$–$C_4$-alkoxycarbonyl, $CONH_2$, chlorine or bromine, or trifluoromethyl.

Aryl is, in particular, phenyl which is optionally substituted by $C_1$–$C_4$-alkyl, trifluoromethyl, chlorine, bromine, carboxyl, cyano, $C_1$–$C_4$-alkoxycarbonyl or $C_1$–$C_4$-alkoxy.

Aralkyl is, in particular, phenyl-$C_1$–$C_4$-alkyl, which can be further substituted in the phenyl nucleus by chlorine, methyl or methoxy.

The preparation of compounds of the formula I wherein
- Y represents a 1,2,4-oxadiazole, 1,3,4-oxadiazole or 1,2,3-triazole radical, a benzoxazole radical which is optionally substituted by 1 or 2 $C_1$–$C_4$-alkyl groups, $C_1$–$C_4$-alkoxy, 1 or 2 chlorine atoms, benzyl, phenyl, cyclohexyl, $C_1$–$C_4$-alkylsulphonyl or $C_1$–$C_4$-alkoxycarbonyl, or a benzo(b)-furan, benzo-s-triazole, naphtho-triazole, 5-phenyl-1,3,4-oxadiazole, 5-phenyl-1,2,4-oxadiazole or 3-phenyl-1,2,4-oxadiazole radical, R represents hydrogen, $C_1$–$C_6$-alkyl which is optionally substituted by $C_1$–$C_4$-alkoxy, hydroxyl, chlorine or cyano, or phenyl and n denotes 1, is preferred.

The preparation of compounds of the formula I wherein
Y represents the radical of the formula

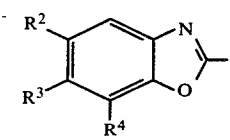

and wherein
n denotes 1,
R² denotes hydrogen, C₁–C₄-alkyl, cyclohexyl, C₁–C₄-alkoxy, chlorine, benzyl, phenyl, C₁–C₄-alkoxycarbonyl or C₁–C₄-alkylsulphonyl,
R³ denotes hydrogen, C₁–C₄-alkyl, chlorine or C₁–C₄-alkoxy and
R⁴ denotes hydrogen, C₁–C₄-alkyl or chlorine, is particularly preferred.

The compounds of the formula V required as starting materials for the rearrangement according to the invention have not yet been described in the literature.

However, these compounds are easily obtained by reacting compounds of the formula

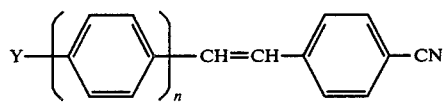
(VI)

with metal azides in polar organic solvents to give compounds of the formula

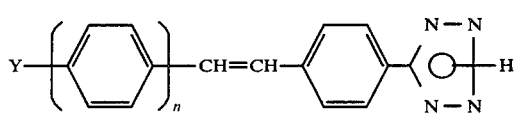
(VII)

and treating these with compounds of the formula

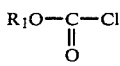

Only some of the compounds of the formula VI are known. They are obtained in a conventional manner, for example by reacting compounds of the formula

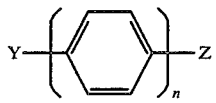
(VIII)

wherein
Z represents a grouping of the formula

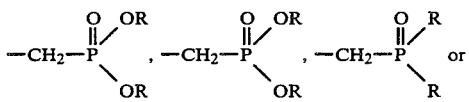 or

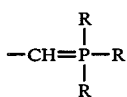

wherein
R denotes C₁–C₄-alkyl, cyclohexyl or phenyl, with p-cyanobenzaldehyde (compare German Offenlegungsschrift No. 2,453,355, German Auslegeschrift No. 1,052,405 and Japanese Preliminary Published Application No. 49/85,378).

The reaction of the tetrazole derivatives VII with the acid chlorides can be carried out in the temperature range from 0° to 120° C., preferably at 25°–90° C.

The reaction is advantageously carried out in inert solvents, for example ethers, such as dioxane, tetrahydrofuran or diisopropyl ether, and furthermore in hydrocarbons, such as toluene, xylene, chlorobenzene or 1,2-dichlorobenzene, or in formamides, such as dimethylformamide, dimethylacetamide or dimethylsulphoxide, preferably in the presence of acid acceptors, in particular tertiary organic bases, such as triethylamine, pyridine, dimethylaniline or hexahydrodimethylaniline.

The rearrangement of the compounds V into the compounds I can be achieved merely by heating the substance to beyond its melting point. However, this reaction is advantageously carried out in the presence of a diluent, preferably a polar organic solvent, which is, needless to say, inert towards these substances.

Compounds of the formula I in which R¹ denotes hydrogen are prepared by reacting compounds of the formula V in which R₁ denotes alkyl with acids in polar organic solvents.

Examples of suitable acids are mineral acids, such as hydrochloric acid and sulphuric acid, and sulphonic acids, such as benzenesulphonic acid and p-toluenesulphonic acid.

The rearrangement can, however, also be carried out in non-polar solvents. Nevertheless, it is then advisable to add bases. Either inorganic or organic compounds which are sufficiently soluble in the reaction mixture can be used as the bases. Preferred bases are organic bases, such as, for example, triethylamine, N-methyl- or N-ethyl-piperidine, piperidine, pyrrolidine, 1,4-diazabicyclo[2,2,2]octane (DABCO), morpholine, N-methyl- or N-ethyl-morpholine and N-ethylpyrrolidine, or the like.

Suitable polar solvents are higher-boiling alcohols, such as n-butanol, tert.-butanol, glycol and diethylene glycol, glycol ethers, such as 2-methoxyethanol and 2-ethoxyethanol, nitriles, such as, for example, benzonitrile, and furthermore formamides, such as, for example, dimethylformamide, dimethylacetamide, N-methylpyrrolidone and phosphoric acid tris-dialkylamides, alkyl being, in particular, C₁–C₄-alkyl.

Non-polar solvents which may be mentioned are toluene, xylene, chlorobenzene and dichlorobenzene. The reaction temperatures for the reaction according to the invention are between 100° and 250° C., preferably between 120° and 200° C.

The present invention furthermore relates to new compounds of the formula I, that is to say compounds of the formula I which are not described in the abovementioned German Offenlegungsschrift No. 2,833,470, wherein
R represents C₁–C₄-alkyl, C₂–C₄-chloroalkyl, C₂–C₄-hydroxyalkyl, cyanoethyl or C₁–C₄-alkoxy-C₂–C₄-alkyl.

These brighteners, which are particularly readily accessible by the new process, are distinguished by improved technological properties compared with the nearest comparable known brighteners, such as, for example, a superior brightening effect on polyester fibres.

Particularly preferred compounds of the formula I are those in which

R has the abovementioned meaning and

Y represents a benzoxazole radical, in particular a radical of the formula

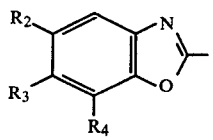

EXAMPLE 1

20.5 g (0.05 mol) of 5-ethoxy-1,3,4-oxadiazol-2-yl-stilbene of the formula

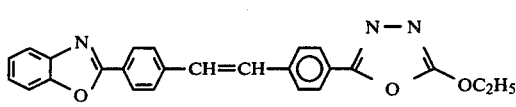

are refluxed in 200 ml of dimethylformamide for 3 hours. After the mixture has been cooled to room temperature, the precipitated product is filtered off, washed with water and methanol and dried at 70° C. in vacuo. 18.5 g (90.4% of theory) of the compound of the formula

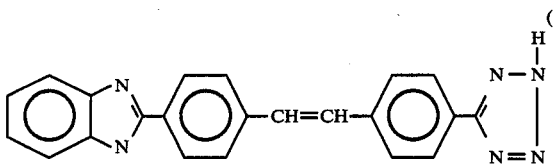

are obtained, and can be recrystallised from dimethylacetamide. Melting point: 284°-85° C.; (absorption: $\lambda max = 366$ nm; IR: $\nu_{C=O} = 1777$ cm$^{-1}$).

| $C_{25}H_{19}N_3O_3$ | (409.5) | C % | H % | N % |
|---|---|---|---|---|
| | calculated | 73.3 | 4.68 | 10.26 |
| | found | 72.8 | 4.6 | 10.0 |

The substance gives brilliant whitening effects on PES in the exhaustion-high temperature process and the thermosol process.

EXAMPLE 2

5.2 g (0.055 mol) of dimethylchlorocarbonate are added to a suspension of 18.3 g (0.05 mol) of 4-(benzoxazol-2-yl)-4'-(1,2,3,4-tetrazol-5-yl)-stilbene (formula 3)

and 5.6 g (0.05 mol) of triethylamine in 200 ml of dimethylacetamide at room temperature. The mixture is then stirred at room temperature for 30 minutes and at 70° C. for 1 hour. The compound of the formula

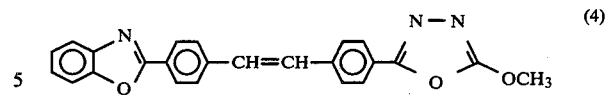

is thereby formed, and is not isolated.

A further 5.5 g of triethylamine are added to the mixture, which is then stirred at 130°-140° C. for 2 hours. After cooling to 20° C., the precipitate is filtered off, washed with water and methanol and dried in vacuo. 15.2 g (76.9% of theory) of light yellow crystals of the compound of the formula

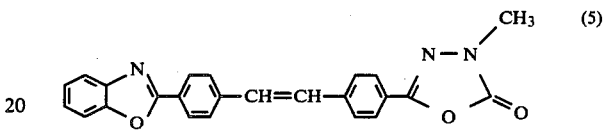

are thus obtained, and can be recrystallised from dimethylformamide. Melting point: 271°-73° C., (absorption: $\lambda max = 360$ nm; IR: $\nu_{CO} = 1776$ cm$^{-1}$). $C_{24}H_{17}N_3O_3$, mass: m/e 395 (63%) M+.

This substance also gives brilliant whitening effects on PES by the exhaustion-high temperature process and the thermosol process.

EXAMPLE 3

Analogously to Example 1, rearrangement of 23 g (0.05 mol) of the compound of the formula

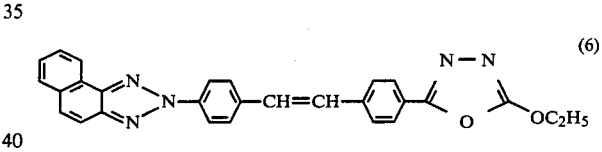

in dimethylformamide gives 17.3 g (75.2% of theory) of a yellow crystalline powder of the compound of the formula

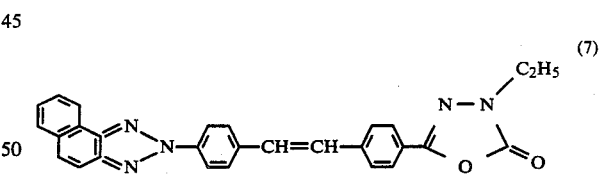

which can be dissolved in and crystallised from dimethylformamide. Melting point: 270°-75° C., (absorption: $\lambda max = 376$ nm, IR: $\nu_{CO} = 1775$ cm$^{-1}$).

| $C_{28}H_{21}N_5O_2$ | (459.5) | C % | H % | N % |
|---|---|---|---|---|
| | calculated: | 73.2 | 4.61 | 15.24 |
| | found: | 72.9 | 4.7 | 15.5 |

EXAMPLE 4

In the same manner as described in Example 1, 22.3 g (0.05 mol) of the methyl derivative (OCH$_3$ instead of OC$_2$H$_5$) of the formula (6) give 21.6 g (96.7% of theory) of light yellow crystals of the formula

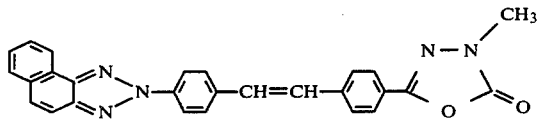

(8)

which can be recrystallised from dimethylformamide. Melting point: 274°–76° C., (absorption: $\lambda max = 376$ nm, IR: $\nu_{CO} = 1776$ cm$^{-1}$).

| $C_{27}H_{19}N_5O_2$ | C % | H % | N % |
|---|---|---|---|
| calculated: | 72.8 | 4.3 | 15.72 |
| found: | 72.2 | 4.4 | 15.9 |

The compound gives outstanding whitening effects with very good fastness properties on PES.

The following compounds are prepared in a manner analogous to that described in Examples 1–4:

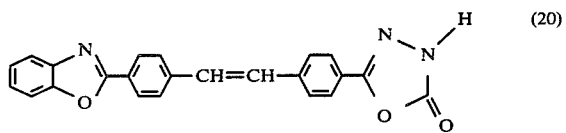

(9)

| No. | Y | Q | Fluorescence in dimethylformamide |
|---|---|---|---|
| 9. | CH$_3$-benzoxazole | CH$_3$ | greenish-tinged violet |
| 10. | Cl-benzoxazole | C$_3$H$_7$—n | reddish-tinged blue |
| 11. | CH$_3$OOC-benzoxazole | CH$_3$ | neutral blue |
| 12. | (CH$_3$)$_3$C-benzoxazole | C$_4$H$_9$—n | blue-violet |
| 13. | CH$_3$O-benzoxazole | CH$_3$ | neutral blue |
| 14. | benzotriazole | CH$_2$CH$_2$ | neutral blue |
| 15. | H,phenyl-triazole | CH$_2$— | reddish-tinged blue |
| 16. | CH$_3$,Ph-triazole | CH$_2$CH$_2$OCH$_3$ | blue |

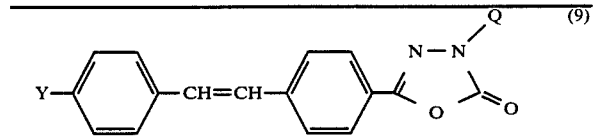

(9)

| No. | Y | Q | Fluorescence in dimethylformamide |
|---|---|---|---|
| 17. | H$_5$C$_2$-N-N(acetyl)(isopropyl) | C$_2$H$_5$ | reddish-tinged blue |
| 18. | CH$_3$O-phenyl | CH$_3$ | neutral blue |
| 19. | biphenyl | C$_4$H$_9$—n | greenish tinged blue |

EXAMPLE 5

50 g of concentrated hydrochloric acid are added dropwise to a suspension of 12.3 g (0.03 mol) of the compound of the formula (1) in 300 ml of dimethylformamide such that a temperature of 25°–30° C. is maintained. The mixture is stirred at 30° C. for 30 minutes and at 60° C. for 3 hours. It is then cooled to room temperature. The product is filtered off and washed with water and methanol. 7.8 g (68.2% of theory) of the compound of the formula

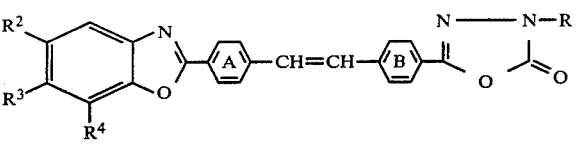

(20)

are obtained in the form of light yellow crystals, which can be recrystallised from dimethylformamide. Melting point: >300° C., (absorption: $\lambda max = 366$ nm, IR: $\nu_{CO} = 1764$ cm$^{-1}$). $C_{23}H_{15}N_3O_3$ (381.4), mass: m/e 381 (85%) M$^+$.

I claim:

1. A compound of the formula

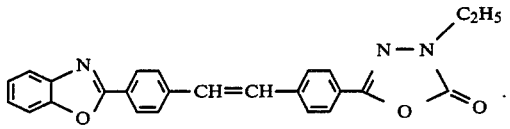

in which
the rings A and B can carry further non-chromophoric substituents,
R is C$_1$–C$_4$-alkyl, C$_2$–C$_4$-chloroalkyl, C$_2$–C$_4$-hydroxyalkyl, cyanoethyl or C$_1$–C$_4$-methoxy-C$_2$–C$_4$-alkyl,
R$^2$ is hydrogen, C$_1$–C$_4$-alkyl, cycloalkyl, C$_1$–C$_4$-alkoxy, chlorine, benzyl, phenyl, C$_1$–C$_4$-alkoxycarbonyl or C$_1$–C$_4$-alkylsulphonyl,
R$^3$ is hydrogen, C$_1$–C$_4$-alkyl, chlorine or C$_1$–C$_4$-alkoxy, and
R$^4$ is hydrogen, C$_1$–C$_4$-alkyl or chlorine.

2. A compound according to claim 1 of the formula

* * * * *